United States Patent [19]

Weithmann

[11] 4,333,948

[45] Jun. 8, 1982

[54] PHARMACEUTICAL FORMULATIONS CONTAINING PROSTAGLANDIN

[75] Inventor: Klaüs U. Weithmann, Eppstein, Fed. Rep. of Germany

[73] Assignee: Hoechst Aktiengesellschaft, Frankfurt am Main, Fed. Rep. of Germany

[21] Appl. No.: 243,443

[22] Filed: Mar. 13, 1981

[30] Foreign Application Priority Data

Mar. 15, 1980 [DE] Fed. Rep. of Germany ....... 3010002

[51] Int. Cl.$^3$ .................... A61K 31/34; A61K 31/215; A61K 31/19

[52] U.S. Cl. .................................... 424/285; 424/274; 424/275; 424/305; 424/317; 424/101; 424/177; 260/112 R

[58] Field of Search ............... 424/305, 317, 274, 285, 424/275

[56] References Cited

U.S. PATENT DOCUMENTS 4,113,882  9/1978  Okazaki et al. ..................... 424/317

*Primary Examiner*—Sam Rosen
*Attorney, Agent, or Firm*—Curtis, Morris & Safford

[57] ABSTRACT

What are disclosed are: a substance, obtained from blood serum and having a molecular weight below 2000, which is suitable for stabilizing prostaglandins, especially those of the A, E, F, or I type; methods for preparing such a stabilizing substance from blood serum; pharmaceutical preparations containing a prostaglandin or prostaglandin derivative together with such a stabilizing substance; and methods for stabilizing a pharmaceutical preparation containing a prostaglandin or prostaglandin derivative.

8 Claims, 1 Drawing Figure

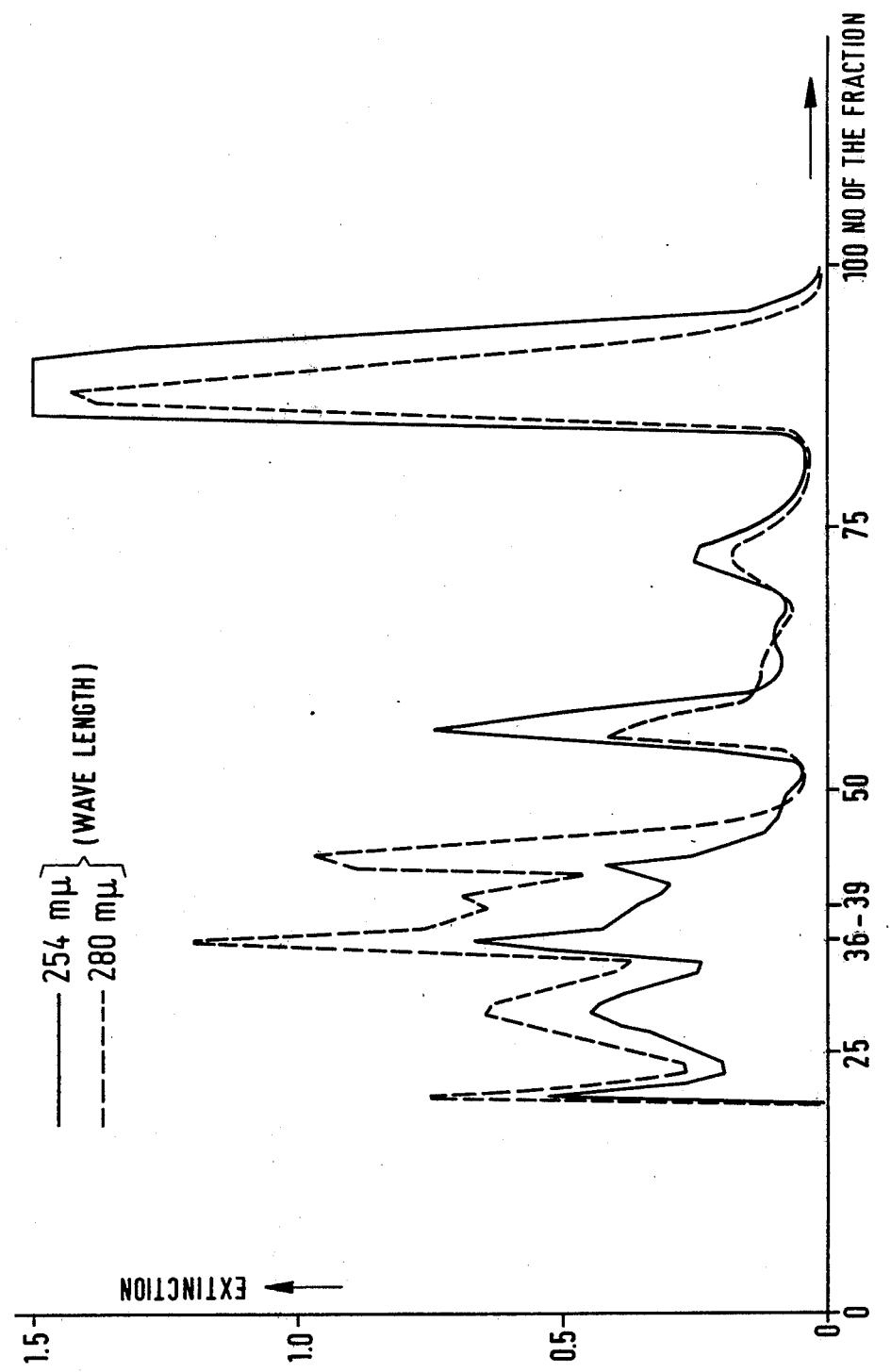

PHARMACEUTICAL FORMULATIONS CONTAINING PROSTAGLANDIN

Prostaglandins, their preparation, and their pharmacological effects are known (cf. the survey in "Chemistry, Biochemistry and Pharmacological Activity of Prostanoids", Robert and Scheinmann, eds., Pergamon Press, Oxford, 1st ed. 1979; Ann. Rev. Biochem. 47, [1978] 997–1029).

Prostaglandins, especially those of the I Type, have multiple valuable pharmacological activities. Thus, for example, prostaglandin $I_2$ ($PGI_2$) inhibits thrombocyte aggregation very efficiently and causes vasodilation (Nature (London) 263, 6, 663, Prostaglandins 14 (1977) 210). Further well-known and important properties are the uterus-contracting, luteolytic, diuretic, antisclerotic, bronchodilating, heart rate-stabilizing, gastric acid secretion-inhibiting and antithrombotic activities. Accordingly, it has been proved in many laboratories that prostaglandins, preferably $PGI_2$, have an excellent pharmacological effect, for example in the cases of arteriosclerosis, ulcers of the gastrointestinal tract, cycle irregularities, hypertension, thromboses, cardiac infarction and apoplexy (Federation Proceedings 38 (1979) 64–93). Only recently, it was demonstrated that patients suffering from painful advanced arteriosclerosis of the lower extremities can be successfully treated with $PGI_2$ (Lancet, May 26, 1979, 1111).

However, in many cases the medically interesting prostaglandins do not have the stability required for medicament formulation. The half-life of $PGI_2$, for example, at physiological pH and room temperature is only a few minutes. Although the stability of $PGI_2$ is improved in a strongly alkaline medium (Prostaglandins 15 (1978), 943), a therapeutic application, for example intravenous or intramuscular administration, of these alkaline solutions is impossible.

As can be concluded from German Offenlegungsschriften Nos. 2,801,846; 2,809,733 and 2,900,352, it is the object of extensive and far-reaching studies to stabilize prostaglandins by chemical modification while maintaining their pharmacological activity.

Another method, that is providing improved stability by a special pharmaceutical composition, is described in German Offenlegungsschrift No. 2,900,428. The stabilizing formulation indicated there comprises prostaglandins as an active substance together with hydrogenated starch hydrolysate consisting of at least 85% of oligo- and polysaccharides, and/or nonionic esters the alcohol component of which is polyethyleneglycol. However, it is known that such unphysiological additives, on repeated parenteral administration, can cause incompatibility reactions in the human organism. Furthermore, cell damage such as hemolysis or undesirable cell fusion must be anticipated from substances having a detergent action. A therapeutic formulation would therefore be welcome which is tolerated by the human organism without any reactions.

It has now been found that a low molecular weight fraction having excellent prostaglandin-stabilizing properties can be obtained from blood serum, preferably from human blood if it is to be used in man.

The present invention thus relates to a low molecular weight fraction of blood serum having a molecular weight below 2,000, preferably below 1,000, which stabilizes prostaglandins, especially of the A, E, F or I type.

The invention further relates to a process for preparing such a stabilizing fraction, which process comprises separating the high molecular weight components from blood serum and obtaining the stabilizing substance by isolation of a fraction having a molecular weight from 0 to 2,000, preferably from 0 to 1,000, Daltons.

Moreover, the invention especially relates to a therapeutic composition wherein the prostaglandins of the A, E, F or I type present are stabilized by a fraction of blood serum having a molecular weight below 2,000, preferably below 1,000.

The prostaglandin-stabilizing, low molecular weight fraction can be obtained from blood serum according to known methods, for example ion-exchange or distribution chromatography or chromatography on molecular sieves; or according to standard methods of protein precipitation, for example precipitation by means of inorganic salts, polyethyleleneglycol or organic solvents; or by electrophoretic methods.

Preferably, first the high molecular weight components of the blood serum are separated according to one of the above methods, especially by precipitation or the use of molecular sieves, and the stabilizing fraction having a molecular weight below 2,000, preferably below 1,000, Daltons is separated from the remaining low molecular weight fraction according to one of the cited methods, for example by chromatography on suitable molecular sieves.

The low molecular weight substance in accordance with the invention is soluble in polar solvents, such as water, methanol, ethanol or dioxane. It is stable to heat and alkalis, is non-volatile, but is unstable to acids.

Stability to a temperature of up to 100° C. can be proved by maintaining the active substance dissolved in water for 5 minutes in a water bath containing boiling water. After this test, the substance possesses its prostaglandin-stabilizing property as before.

When an aqueous solution of the active substance is adjusted with 1 N NaOH at 25° C. to pH 12, kept for 5 minutes at this pH, and subsequently readjusted to neutral with 1 N HCl, the stabilizing action is maintained intact.

The prostaglandin-stabilizing property of the active substance is likewise maintained if an aqueous solution of the stabilizer is lyophilized, the stabilizer is left in the lyophilized state for 3 hours at 25° C. and 1 mm Hg, and is then redissolved in water. On the other hand, the prostaglandin-stabilizing property is lost when an aqueous solution containing the active ingredient is adjusted with 1 N HCl at 25° C. to pH 1.5, left for 10 minutes at this pH, and readjusted to neutral with 1 N NaOH.

Typical prostaglandins the stability of which can be considerably increased in the form of a pharmaceutical formulation are, for example, compounds having the following ring structures of the prostaglandin molecule:

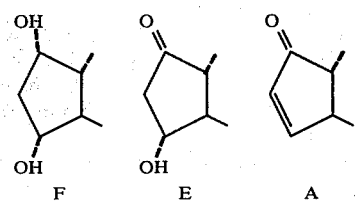

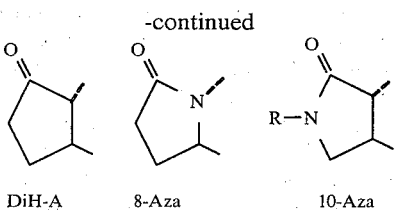

DiH-A   8-Aza   10-Aza having an upper side chain of the formula

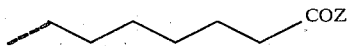

which is optionally substituted by alkyl or has cis-double bonds in the 4- or 5-position or trans-double bonds in the 2- or 2,4-position, or a keto group in the 6-position, in which formula Z is hydroxy, $C_{1-10}$-alkoxy or a physiologically tolerable cation, and having a lower side chain of the formula

in which Y is hydrogen or alkyl and R, for example, $C_{1-8}$-alkyl, cycloalkyl, haloalkyl or alkoxyalkyl.

Especially prostacyclin and analogs or derivatives of prostacyclin can be stabilized according to the invention, for example those of the formula

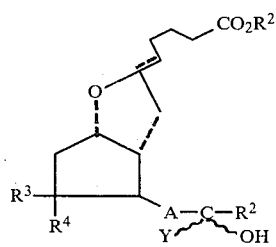

in which
$R^1$ is hydrogen, a linear or branched, saturated or unsaturated aliphatic hydrocarbon radical having up to 8 carbon atoms, a cycloaliphatic hydrocarbon radical having from 3 to 7 carbon atoms, an araliphatic hydrocarbon radical having 7 to 9 carbon atoms, or a physiologically tolerable metal ion, $NH_4$ ion or ammonium ion derived from a primary, secondary or tertiary amine, or a tetraalkylammonium ion;
$R^2$ is a cycloaliphatic hydrocarbon radical having from 3 to 7 carbon atoms or a linear or branched, saturated or unsaturated aliphatic hydrocarbon radical having up to 8 carbon atoms, which may be substituted
 (a) by an alkoxy or alkenyloxy radical having up to 6 carbon atoms,
 (b) by a cycloalkyl or cycloalkoxy radical having from 3 to 7 carbon atoms,
 (c) by halogen or an α- or β-thienyl radical or an α- or β-furyl radical which in turn can be mono- to trisubstituted in the nucleus by halogen, $CF_3$ and/or alkyl or alkoxy each having from 1 to 6 carbon atoms, or
 (d) a phenyl, oxyphenyl or an α- or β-oxythienyl radical which in turn can be mono- to trisubstituted in the nucleus by halogen, for example chlorine or bromine, $CF_3$ and/or alkyl or alkoxy each having from 1 to 6 carbon atoms;
Y is hydrogen or alkyl;
$R^3$ and $R^4$ together are oxygen or

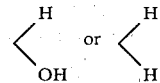

and
A is a trans

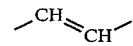

group or a $—CH_2—CH_2$ group.

Preferably, those prostacyclin derivatives of formula I can be stabilized wherein $R^2$ is a radical of the formula

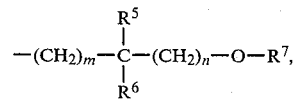

in which $R^5$ and $R^6$, which may be identical or different, each are hydrogen or a methyl or ethyl group, and $R^7$ is a linear or branched alkyl radical having from 1 to 5 carbon atoms or a cycloalkyl radical having from 5 to 7 carbon atoms, and m and n, which may be identical or different, each are 0, 1, 2 or 3; the total number of carbon atoms in the radical of the formula II being from 3 to 10: or where $R^2$ is a cycloalkyl radical having from 5 to 7 carbon atoms, or a linear or branched alkyl radical having from 1 to 5 carbon atoms, which may be substituted by
 (a) fluorine or chlorine, or an α- or β-thienyl radical, or an α- or β-furyl radical, which in turn may be substituted by halogen, trifluoromethyl and/or alkyl or alkoxy each having from 1 to 6 carbon atoms;
 (b) an oxyphenyl or an α- or β-oxythienyl radical, which in turn may be mono- to trisubstituted in the nucleus by halogen, trifluoromethyl and/or alkyl or alkoxy each having from 1 to 6 carbon atoms;
and where A is the trans

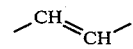

group, Y is hydrogen and $R^3$ and $R^4$ are

Further prostacyclin analogs which have a more specific action and/or a longer period of action than $PGI_2$ can be stabilized according to the invention. These analogs have the formula

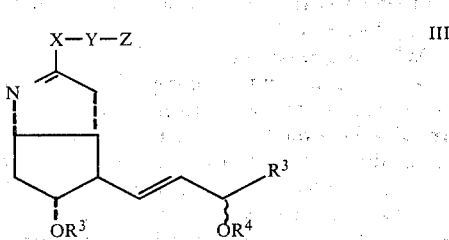

III wherein:
X is an oxygen or sulfur atom or an NH group,
Y is a straight-chain or branched alkylene radical having up to 8 carbon atoms, a straight-chain or branched, saturated or unsaturated aliphatic radical having 3 to 8 carbon atoms, a cycloaliphatic radical having 3 to 6 carbon atoms or a phenylene radical,
Z is a radical of the formula $-CO_2R^1$, $-CH_2OH$ or $CH_2N(R^2)_2$, wherein
$R^1$ is hydrogen, a straight-chain or branched alkyl radical having up to 8 carbon atoms, a straight-chain or branched unsaturated aliphatic hydrocarbon radical having 3 to 7 carbon atoms, a cycloaliphatic hydrocarbon radical having 3 to 7 carbon atoms, an araliphatic hydrocarbon radical having 7 to 9 carbon atoms or a physiologically acceptable metal ion, $NH_4$ ion or an ammonium ion derived from a primary, secondary or tertiary amine, or a tetraalkylammonium ion,
$R^2$, taken alone, is hydrogen or a straight-chain or branched aliphatic hydrocarbon radical having up to 5 C atoms, the two $R^2$ groups, taken together, are a $-(CH_2)_n-$group with $n=3-6$,
$R^3$ is an aryl radical which can be monosubstituted to trisubstituted in the nucleus by halogen, trifluoromethyl and/or alkyl or alkoxy each having 1-6 C atoms, or a cycloaliphatic radical having 3-8 carbon atoms or a straight-chain or branched alkyl radical having up to 8 carbon atoms or a straight-chain or branched unsaturatd aliphatic hydrocarbon radical having 3 to 8 carbon atoms, which radicals can be in turn be substituted by
(a) a straight-chain or branched alkoxy radical having up to 6 carbon atoms or a straight-chain or branched alkenyloxy or alkynyloxy radical having 3 to 6 carbon atoms,
(b) halogen, phenyl or an α- or β-thienyl or α- or β-furyl radical which in turn can be monosubstituted to trisubstituted in the nucleus by halogen, trifluoromethyl and/or alkyl or alkoxy each having 1-6 C atoms, or
(c) a phenoxy radical, an α- or β-thienyloxy radical or a cycloalkoxy radical having 3 to 7 carbon atoms, it being possible for the said radicals to be in turn monosubstituted to trisubstituted in the nucleus by halogen, trifluoromethyl and/or alkyl or alkoxy having 1 to 6 C atoms, and
$R^4$ and $R^5$ are identical or different protective groups which can readily be eliminated under neutral or basic conditions.

The low molecular weight active substance according to the invention is characterized by its efficacy to stabilize prostaglandins, especially those of the I type. The stabilization can be tested by determining the amount of remaining prostaglandin and the amount of decomposition products after a storage time of from 1 hour to 7 months at a storage temperature of 70°, 50°, 25° and 0° C. in known manner, for example by thin-layer chromatography. Moreover, the formulation containing prostaglandins, preferably those of the E or I type, can be tested with respect to its pharmacodynamic action, for example as an inhibitor of arachidonic acid-induced thrombocyte aggregation in human plasma by determining the incidence of an aggregation-inhibiting effect in intervals of 2 hours with the use of a formulation according to the invention containing an aggregation-inhibiting amount of prostaglandin, for example $10^{-7}$ M to $10^{-9}$ M of $I_2$-type prostaglandin.

The weight ratio of the prostaglandins, especially those of the I type, to be stabilized and the active substance of the invention is advantageously from about $1:10^6$ to about $1:10^2$, preferably about $1:10^4$. The prostaglandins are used in the form of a water-soluble salt, for example the Na salt or the tromethamine salt, or in the form of a physiologically acceptable ester.

The therapeutically effective composition is prepared by adding the stabilizing low molecular weight fraction, for example in the form of an eluate after column chromatography, to an aqueous solution of a prostaglandin, preferably in the form of a prostacyclin salt (for example 200 ml of the eluate to 20 ml of a $10^{-5}$ to $10^{-7}$ molar aqueous prostaglandin solution), and adjusting the pH to 6.5-8.5, preferably to 7.3. Alternatively, operations may be as follows: the water is removed from the eluate, for example by evaporation, rotation or lyophilization; a solution having the intended concentration is prepared from the solid active substance using distilled water; and this solution is mixed in the desired ratio with an aqueous prostaglandin solution. The solution so obtained can be used for infusions or injections, but alternatively may be lyophilized and then given a unit dosage form for enteral administration, for example tablets or capsules.

The compositions according to the invention have the same pharmacological activity as the prostaglandins contained therein. The formulation is administered in an amount which contains the quantity of prostaglandin required for producing the intended effect.

The following examples illustrate the invention.

EXAMPLE 1

100 ml of human serum are filtered through a filter UM2 (Amicon, Witten/Ruhr) in a commercially available stirred cell.

The filtrate is lyophilized and the residue is introduced into 10 ml of bidistilled water. After centrifugation for 15 minutes at 4,500 rpm, the colorless to light yellow supernatant is introduced onto a column K16/100 (Pharmacia, Uppsala) containing the packing 87.5 cm × 1.6 cm P2 (Biorad GmbH, Munich). Elution is carried out with distilled water. The elution rate is about 35 ml/100 minutes. Each fraction contains about 3.5 ml.

The low molecular weight fractions No. 36 to 39, corresponding to a $K_{av}$ value of 0.38 (Laurent, Killander, J. Chromatogr. 14 (1964) 317) (see the accompanying Drawing), after rotation at 30°-35° C. yield about 0.6 g of an active substance which can be used for stabilizing prostaglandins, especially prostacyclin and the derivatives thereof.

EXAMPLE 2

33 ml of human serum and 33 ml of a 1:1 (w/v) mixture of polyethyleneglycol 6000 (Merck, Darmstadt) and water are stirred for 20 minutes at 0° C., and subsequently centrifuged for 20 minutes in a Rotor Sorvall SS 34 (DuPont de Nemours, Bad Nauheim) at 20,000 rpm. The supernatant (54 ml) is liberated from high molecular weight components (dialysis membranes UM2, Amicon, Witten/Ruhr). After lyophilization, the residue is introduced into 6 ml of distilled water, and 1 ml thereof is introduced onto a column K 9/30 (Pharmacia, Uppsala) packed with 28 cm×0.9 cm Sephadex G10 (Pharmacia, Uppsala). Elution is carried out with the use of a 0.9% sodium chloride solution. The elution rate is 23 ml/60 min. Each fraction contains 1 ml. Fractions 10 to 15, suitable as a stabilizer according to the invention, appear immediately after the exclusion volume corresponding to a $K_{av}$ value of 0.05.

EXAMPLE 3

10 to 20 μl of a $10^{-5}$ to $10^{-7}$ M aqueous solution of the Na salt of prostacyclin are added to 200 μl of the stabilizer fraction (obtained according to Example 1). The solution is adjusted to pH 7.3 and heated for several hours at 50° C. Subsequently, the effect of the stabilizer is tested by determining, in the usual manner, the inhibition of thrombocyte aggregation by the formulation.

EXAMPLE 4

10 to 20 μl of a $10^{-5}$ to $10^{-7}$ M aqueous solution of the Na salt of prostacyclin are added to 200 μl of the stabilizer fraction and the mixture of solutions is adjusted to pH 7.3 and lyophilized. The lyophilized mixture is processed to tablets or capsules. Alternatively, it can be used for storing the formulation, and, as needed, converted with 210 to 220 μl of distilled water to a ready-to-use solution.

What is claimed is:

1. A pharmaceutical composition comprising an effective amount of a prostaglandin or prostaglandin derivative in admixture with a substance stabilizing prostaglandins, which substance is a blood serum fraction having a molecular weight below 2000 which is stable to alkalis, is unstable to acids, is stable to temperatures up to 100° C., and is non-volatile at room temperature.

2. A composition as in claim 1 wherein said stabilizing substance has a molecular weight below 1000.

3. A composition as in claim 1 wherein said prostaglandin or derivative is a prostaglandin of the I type or a derivative thereof.

4. A composition as in claim 1 wherein the ratio by weight of prostaglandin or derivative to the stabilizing substance is from about $1:10^6$ to $1:10^2$.

5. A method for stabilizing a pharmaceutical preparation containing a prostaglandin or a prostaglandin derivative which method comprises mixing said preparation with a blood serum fraction having a molecular weight below 2000 and which is stable to alkalis, is unstable to acids, is stable to temperatures up to 100° C., and is non-volatile at room temperature.

6. A method as in claim 5 wherein said blood serum fraction has a molecular weight below 1000.

7. A method as in claim 5 wherein said prostaglandin or derivative is a prostaglandin of the I type or a derivative thereof.

8. A method as in claim 5 wherein the ratio by weight of prostaglandin or derivative to the blood serum fraction is from about $1:10^6$ to $1:10^2$.

* * * * *